(12) United States Patent
Thompson

(10) Patent No.: US 11,554,973 B2
(45) Date of Patent: Jan. 17, 2023

(54) INLINE DRAIN SANITIZING SYSTEM

(71) Applicant: Drain Guard, Inc., Bradenton, FL (US)

(72) Inventor: Todd E. Thompson, Bradenton, FL (US)

(73) Assignee: Drain Guard, Inc., Bradenton, FL (US)

( * ) Notice: Subject to any disclaimer, the term of this patent is extended or adjusted under 35 U.S.C. 154(b) by 0 days.

(21) Appl. No.: 17/696,647

(22) Filed: Mar. 16, 2022

(65) Prior Publication Data
US 2022/0340457 A1  Oct. 27, 2022

Related U.S. Application Data

(63) Continuation-in-part of application No. 17/236,805, filed on Apr. 21, 2021.

(51) Int. Cl.
| | |
|---|---|
| B01D 11/02 | (2006.01) |
| B08B 3/00 | (2006.01) |
| E03B 11/00 | (2006.01) |
| B01D 17/06 | (2006.01) |
| C02F 1/50 | (2006.01) |
| C02F 1/32 | (2006.01) |
| A61L 2/18 | (2006.01) |
| A61L 2/23 | (2006.01) |
| F24F 13/22 | (2006.01) |
| F24F 8/22 | (2021.01) |
| A61L 2/10 | (2006.01) |

(52) U.S. Cl.
CPC ............... *C02F 1/505* (2013.01); *A61L 2/10* (2013.01); *A61L 2/18* (2013.01); *A61L 2/23* (2013.01); *C02F 1/32* (2013.01); *F24F 8/22* (2021.01); *F24F 13/222* (2013.01); *A61L 2202/11* (2013.01); *C02F 2303/04* (2013.01)

(58) Field of Classification Search
CPC . A61L 2/0088; A61L 2/18; A61L 2/16; A61L 2/23; A61L 2202/20
USPC ..... 422/261, 263–264; 137/1, 268; 134/133; 210/748.03, 748.1, 748.16
See application file for complete search history.

(56) References Cited

U.S. PATENT DOCUMENTS

| | | | | |
|---|---|---|---|---|
| 4,844,828 | A * | 7/1989 | Aoki .................... | C08F 8/48 525/61 |
| 6,138,703 | A * | 10/2000 | Ferguson ............ | F16K 3/0227 137/268 |
| 2020/0340707 | A1* | 10/2020 | Italia .................... | C02F 1/688 |
| 2021/0239356 | A1* | 8/2021 | Thompson ............ | C02F 1/688 |

* cited by examiner

*Primary Examiner* — Monzer R Chorbaji
(74) *Attorney, Agent, or Firm* — Brian J. Colandreo; Jeffery T. Placker; Holland & Knight LLP

(57) ABSTRACT

An inline drain sanitizing system, includes: a manifold assembly including an inlet port, an outlet port, and a treatment port, wherein: the inlet port is configured to be couplable to a condensate supply line and receive unsanitized condensate, and the outlet port is configured to be couplable to a condensate drain line and provide sanitized condensate; and a treatment subsystem configured to interface with the treatment port and process the unsanitized condensate to generate the sanitized condensate.

29 Claims, 10 Drawing Sheets

INLINE DRAIN SANITIZING SYSTEM

RELATED APPLICATION(S)

This application is a Continuation-in-Part of U.S. application Ser. No. 17/236,805, filed 21 Apr. 2021, the entire contents of which are hereby incorporated by reference in its entirety.

TECHNICAL FIELD

This disclosure relates generally to inline drain sanitizing systems, and more particularly to inline drain sanitizing systems for use with air conditioning systems.

BACKGROUND

Air-conditioning systems are ubiquitous in the United States for both residential and commercial use. However and when in continuous use, air-conditioning drain lines may develop internal-growth bacteria, algae, and/or fungus, which may cause the drain to become clogged and thereby cause damage to housing parts and structures, and also cause emission of unpleasant odors.

SUMMARY OF DISCLOSURE

In one implementation, an inline drain sanitizing system, includes: a manifold assembly including an inlet port, an outlet port, and a treatment port, wherein: the inlet port is configured to be couplable to a condensate supply line and receive unsanitized condensate, and the outlet port is configured to be couplable to a condensate drain line and provide sanitized condensate; and a treatment subsystem configured to interface with the treatment port and process the unsanitized condensate to generate the sanitized condensate.

One or more of the following features may be included. The manifold assembly may be constructed of a transparent material to allow for the monitoring of condensate flow. The treatment subsystem may be configured to be removably attachable to the manifold assembly. The treatment subsystem may be configured to be threadably attachable to the manifold assembly. The treatment subsystem may be configured to utilize a chemical-based treatment system to sanitize the unsanitized condensate. The chemical-based treatment system may be configured to contain a sanitizing composition. The sanitizing composition may be contained within a dissolvable bag. The treatment subsystem may be configured to allow the unsanitized condensate to interact with the sanitizing composition to generate the sanitized condensate. The treatment subsystem may be constructed of a transparent material to allow for the monitoring of the sanitizing composition. The sanitizing composition may include silver nitrate. The sanitizing composition may include one or more of: a powered sanitizing composition; a granular sanitizing composition; a solid sanitizing composition; a gel sanitizing composition; and a liquid sanitizing composition. The treatment subsystem may be configured to utilize a light-based treatment system to sanitize the unsanitized condensate. The light-based treatment system may be configured to generate ultraviolet light. The treatment subsystem may be configured to allow the unsanitized condensate to interact with the ultraviolet light to generate the sanitized condensate. The condensate supply line may be configured to be coupled to an air conditioning unit. The condensate drain line may be configured to discharge the sanitized condensate.

In another implementation, an inline drain sanitizing system includes: a manifold assembly including an inlet port, an outlet port, and a treatment port, wherein: the inlet port is configured to be couplable to a condensate supply line and receive unsanitized condensate, and the outlet port is configured to be couplable to a condensate drain line and provide sanitized condensate; and a treatment subsystem configured to interface with the treatment port and process the unsanitized condensate to generate the sanitized condensate; wherein the treatment subsystem is configured to be threadably attachable to the manifold assembly and to utilize a chemical-based treatment system to sanitize the unsanitized condensate.

One or more of the following features may be included. The manifold assembly may be constructed of a transparent material to allow for the monitoring of condensate flow. The chemical-based treatment system may be configured to contain a sanitizing composition. The sanitizing composition may be contained within a dissolvable bag. The treatment subsystem may be configured to allow the unsanitized condensate to interact with the sanitizing composition to generate the sanitized condensate. The treatment subsystem may be constructed of a transparent material to allow for the monitoring of the sanitizing composition. The sanitizing composition may include silver nitrate. The sanitizing composition may include one or more of: a powered sanitizing composition; a granular sanitizing composition; a solid sanitizing composition; a gel sanitizing composition; and a liquid sanitizing composition. The condensate supply line may be configured to be coupled to an air conditioning unit. The condensate drain line may be configured to discharge the sanitized condensate.

In another implementation, an inline drain sanitizing system includes: a manifold assembly including an inlet port, an outlet port, and a treatment port, wherein: the inlet port is configured to be couplable to a condensate supply line and receive unsanitized condensate, and the outlet port is configured to be couplable to a condensate drain line and provide sanitized condensate; and a treatment subsystem configured to interface with the treatment port and process the unsanitized condensate to generate the sanitized condensate; wherein: the treatment subsystem is configured to be threadably attachable to the manifold assembly and to utilize a chemical-based treatment system to sanitize the unsanitized condensate, the condensate supply line is configured to be coupled to an air conditioning unit, and the condensate drain line is configured to discharge the sanitized condensate.

One or more of the following features may be included. The chemical-based treatment system may be configured to contain a sanitizing composition. The sanitizing composition may be contained within a dissolvable bag. The treatment subsystem may be configured to allow the unsanitized condensate to interact with the sanitizing composition to generate the sanitized condensate.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
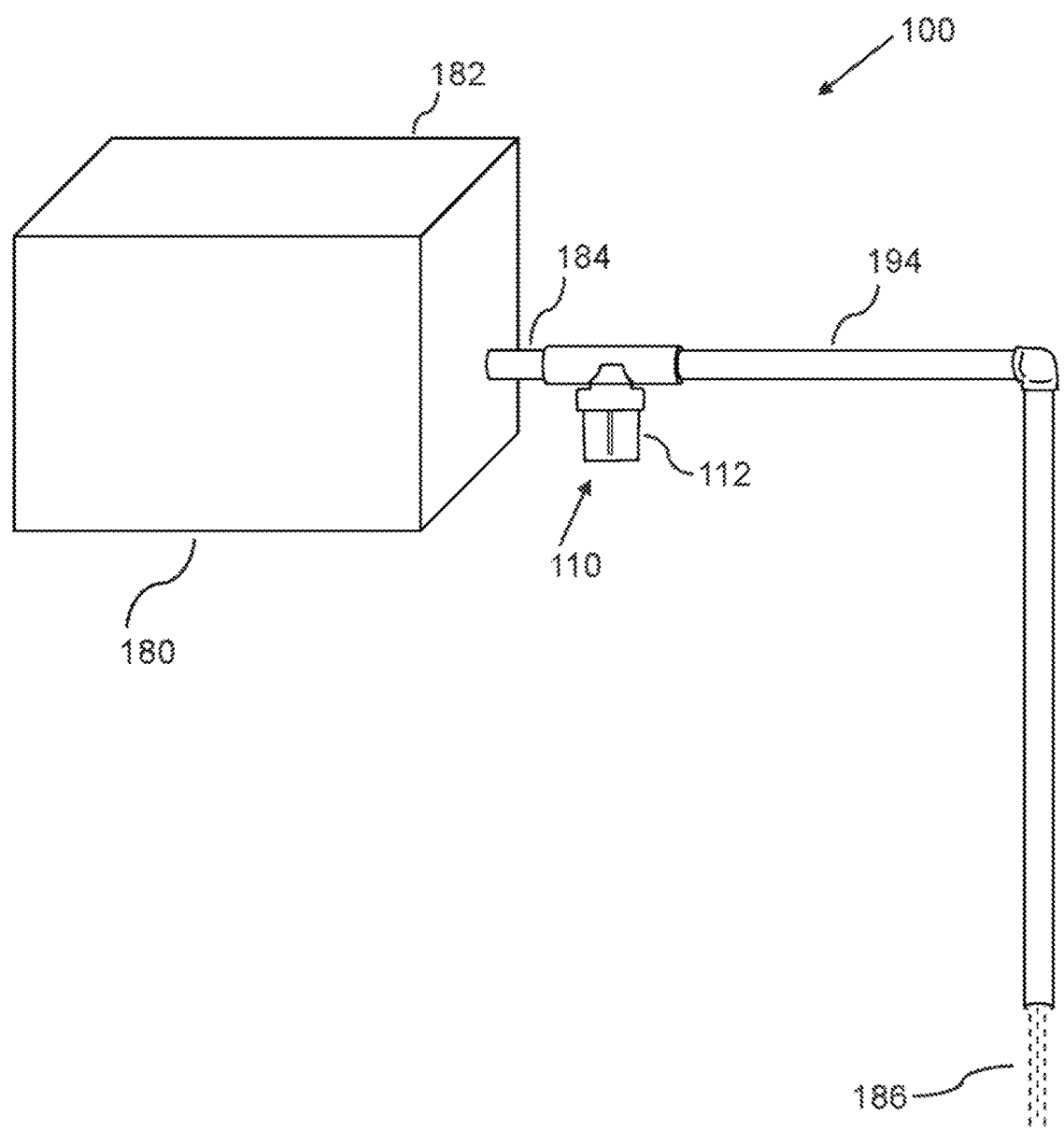
FIG. 1 is a diagrammatic view of an air-conditioning drain line sanitizing system that includes an inline drain sanitizing system according to an embodiment of the present disclosure.
Figure 2:
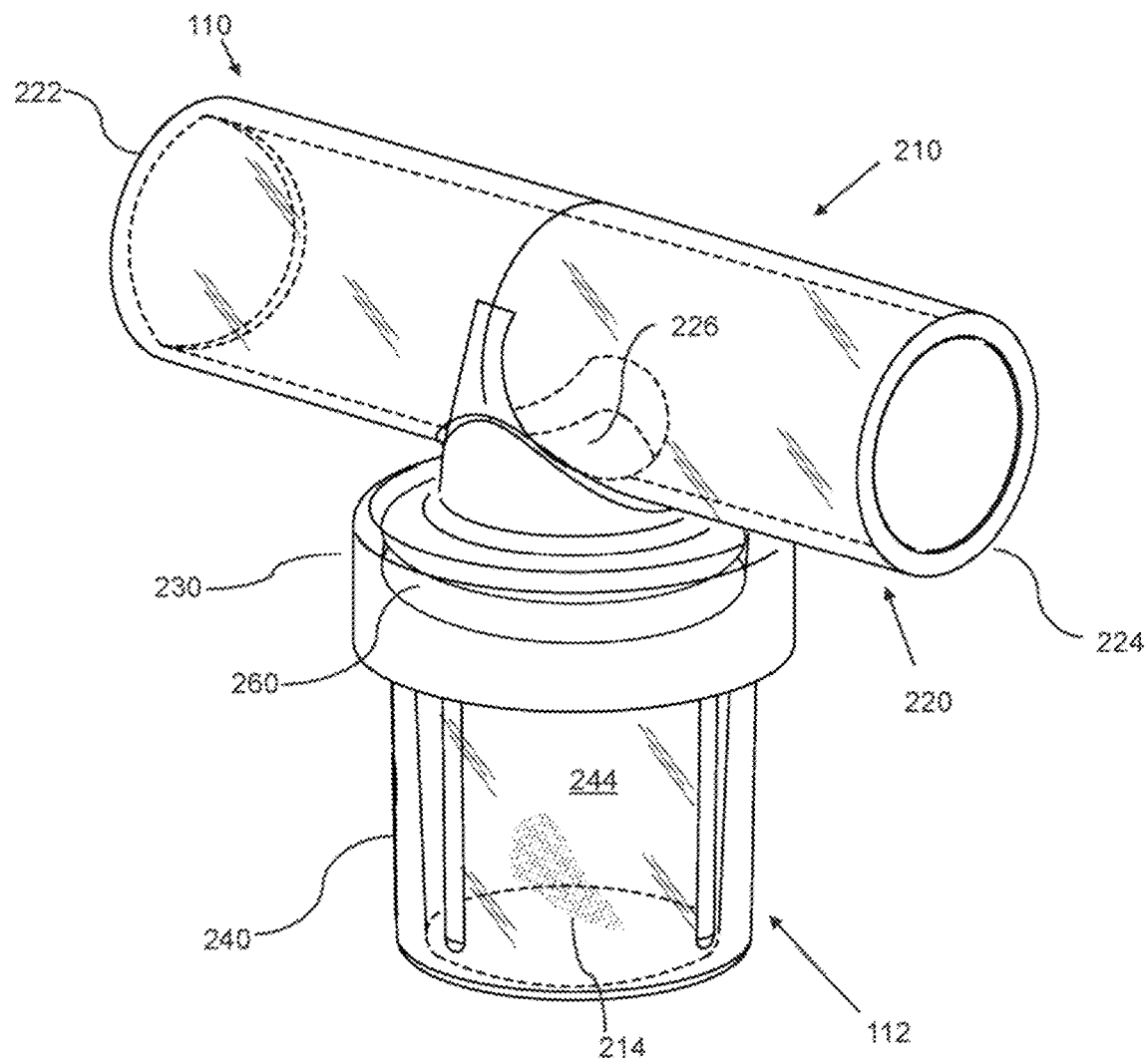
FIG. 2 is a perspective view of the inline drain sanitizing system of FIG. 1 according to an embodiment of the present disclosure.

Referring to FIGS. 1-2, there is shown air-conditioning drain line sanitizing system 100. Air-conditioning drain line sanitizing system 100 may be coupled to air-conditioning unit 180. Air-conditioning unit 180 may include air-conditioning enclosure 182 and condensate supply line 184 positioned on e.g., a side of air conditioning enclosure 182. Condensate supply line 184 may be configured to emit condensate fluid 186 from air-conditioning unit 180 during operation of the air-conditioning unit 180. Air-conditioning drain line sanitizing system 100 may also include condensate drain line 194 that may be configured with a hollow interior to allow condensate fluid 186 to be discharged and flow away from air-conditioning unit 180 via condensate drain line 194.

Air-conditioning drain line sanitizing system 100 may also include inline drain sanitizing system 110 that may include treatment subsystem 112. As will be discussed below in greater detail, treatment subsystem 112 may be configured to utilize a chemical-based treatment system to sanitize unsanitized condensate (e.g., condensate fluid 186). For example, treatment subsystem 112 may include container body 240 that may include sanitizing composition 214. Treatment subsystem 112 may be configured to allow the unsanitized condensate (e.g., condensate fluid 186) to interact with sanitizing composition 214 such that sanitizing composition 214 may sanitize condensate fluid 186 and condensate drain line 194.

Container body 240 may be configured to be detachable from container connector 230 of manifold assembly 210 of inline drain sanitizing system 110. Inline drain sanitizing system 110 may be connected between an outer end of condensate supply line 184 and a first end of condensate drain line 194 to create a fluid connection between condensate supply line 184 and condensate drain line 194. Inline drain sanitizing system 110 may be configured to mix condensate fluid 186 emitted from condensate supply line 184 with sanitizing composition 214 such that sanitizing composition 214 may sanitize condensate fluid 186 and condensate drain line 194. Accordingly, the risk of clogging of condensate drain line 194 may be reduced. Condensate fluid 186 may generally be water, which may contain debris and contaminants. Installation of inline drain sanitizing system 110 may generally not impede the flow rate or performance of condensate drain line 194.

In related embodiments, use of inline drain sanitizing system 110 may not be restricted to use on air-conditioning unit 180, but may be installed in any drain line in any system from which fluids may be emitted. Additionally/alternatively, inline drain sanitizing system 110 may be used for any pipe installation with fluid flow in e.g., the food or chemical industries. Inline drain sanitizing system 110 may be used with gravity fed, low flow, or non-pressurized flow pipe lines.

Inline drain sanitizing system 110 may include manifold assembly 210 (e.g., a tee pipe fitting), such that manifold assembly 210 may include connector pipe segment 220 (including inlet port 222 and outlet port 224) and treatment port 226 in a bottom side of connector pipe segment 220. Container connector 230 may be connected to the bottom side of connector pipe segment 220 proximate treatment port 226. Treatment subsystem 112 may be configured to be removably attachable to container connector 230 via e.g., a snap lock and/or screw on (e.g., threaded) fitting.

Figure 3A:
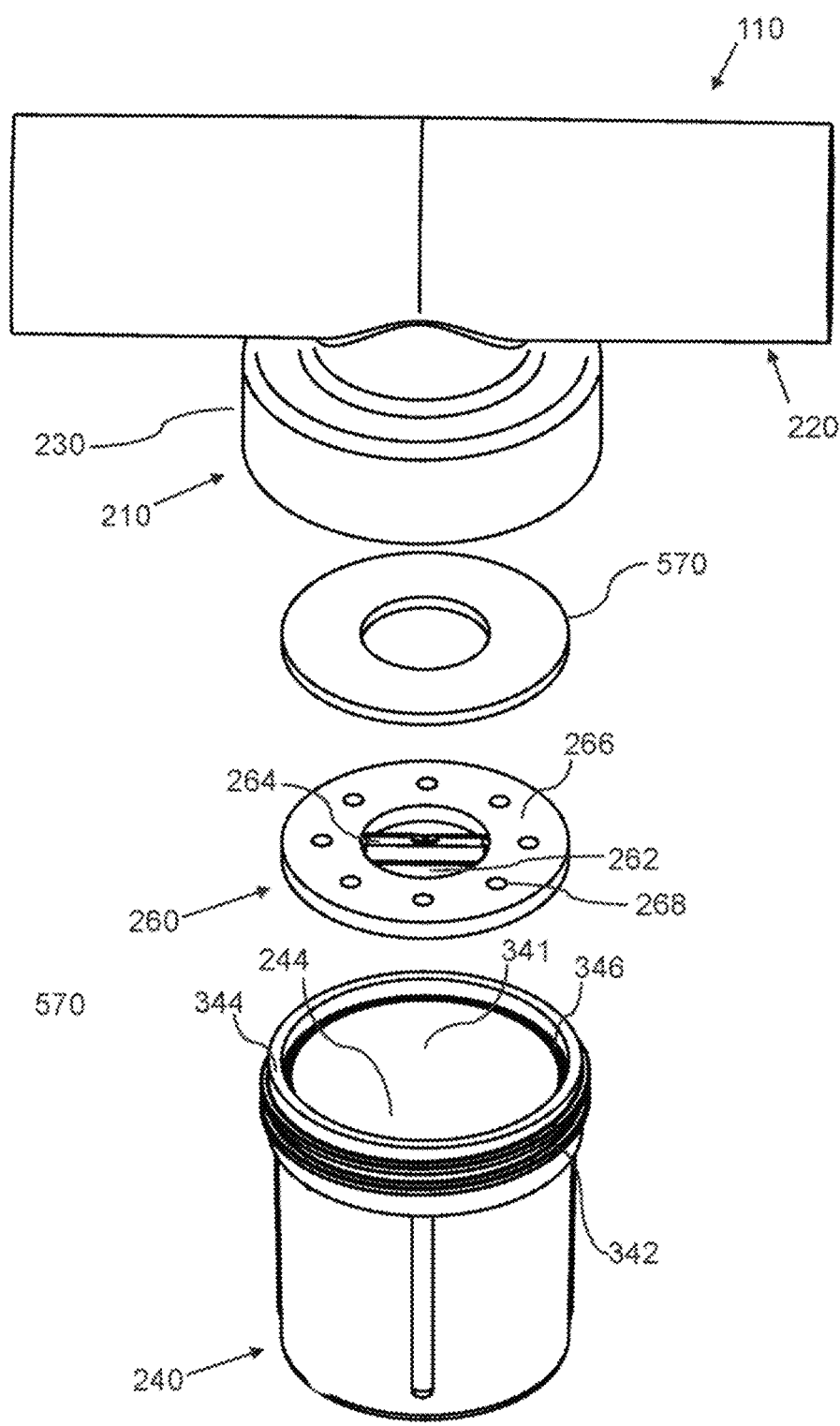
FIG. 3A is a top perspective view of the inline drain sanitizing system of FIG. 1 according to an embodiment of the present disclosure.
Figure 3B:
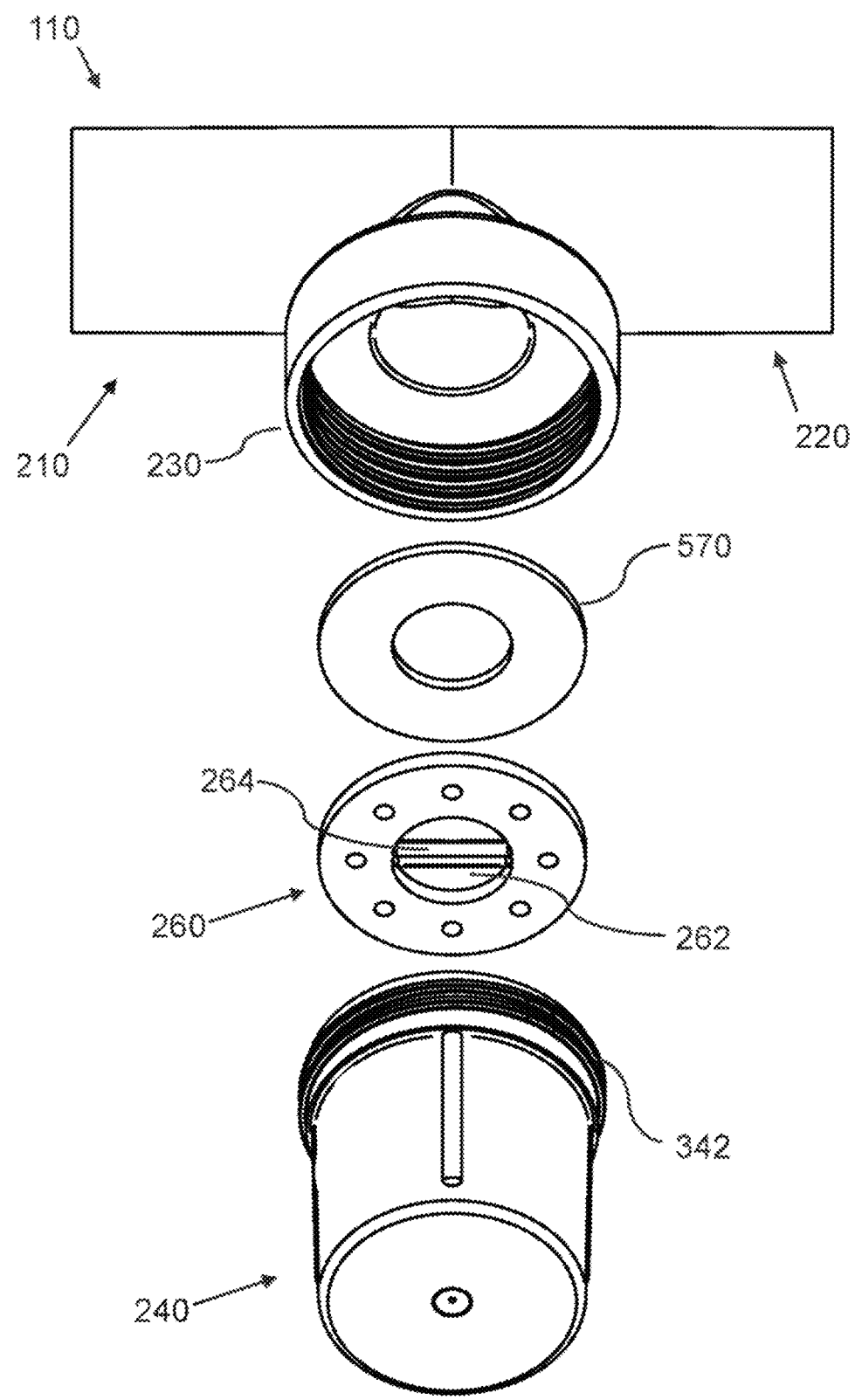
FIG. 3B is a bottom perspective view of the inline drain sanitizing system of FIG. 1 according to an embodiment of the present disclosure.
Figure 3C:
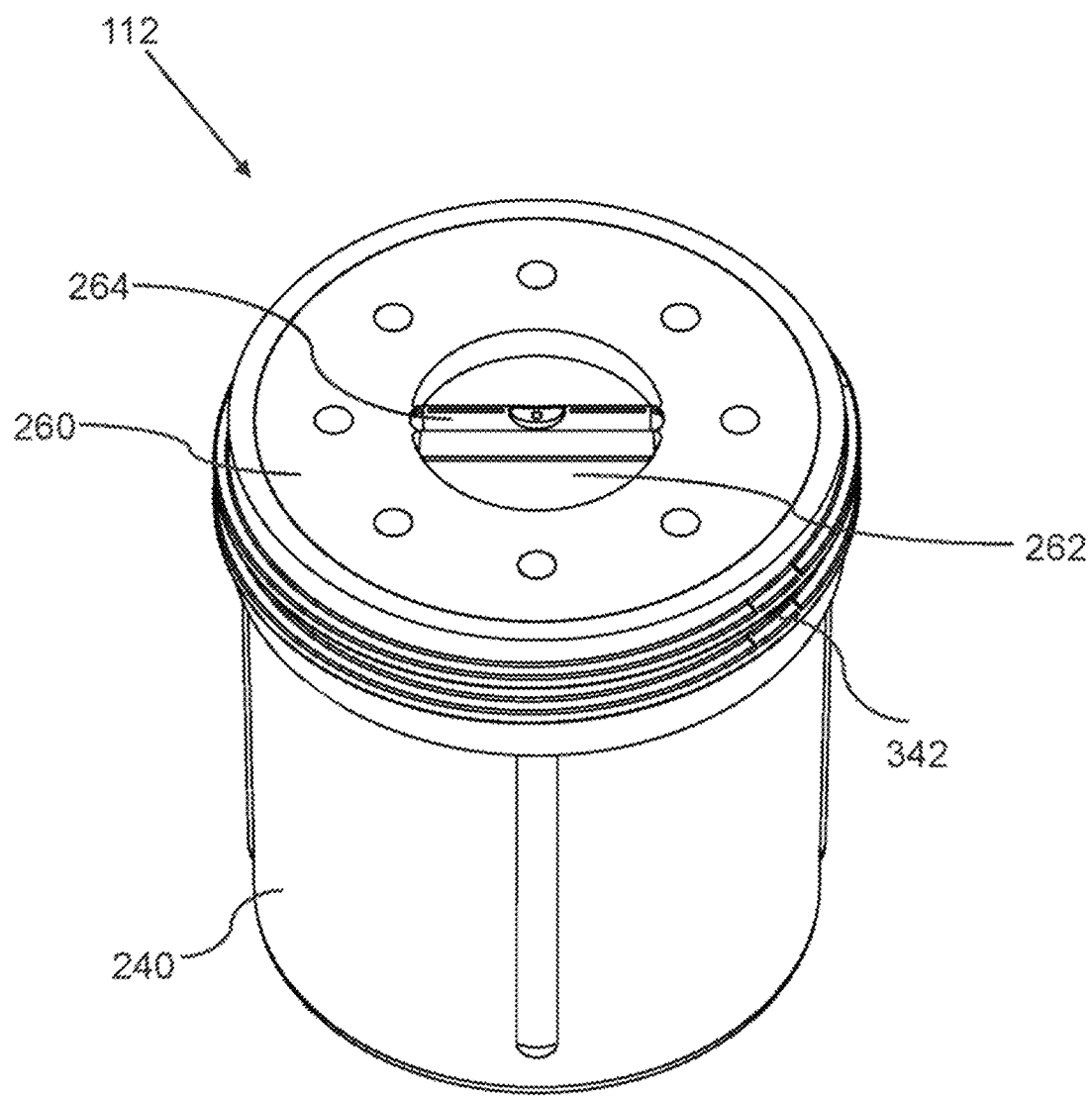
FIG. 3C is a perspective view of a treatment subsystem of the inline drain sanitizing system of FIG. 1 according to an embodiment of the present disclosure.
Figure 4:
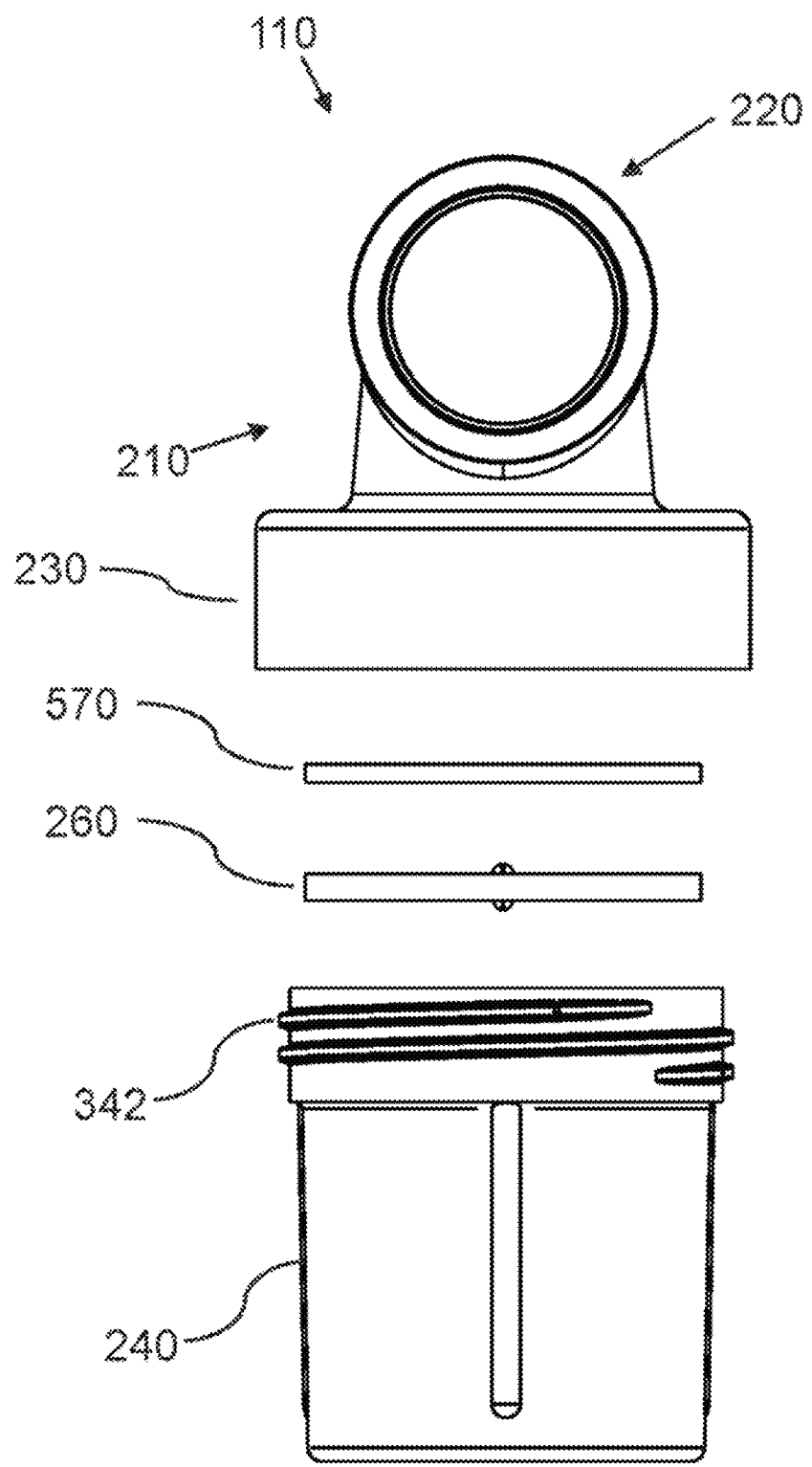
FIG. 4 is a side view of the inline drain sanitizing system of FIG. 1 according to an embodiment of the present disclosure.
Figure 5:
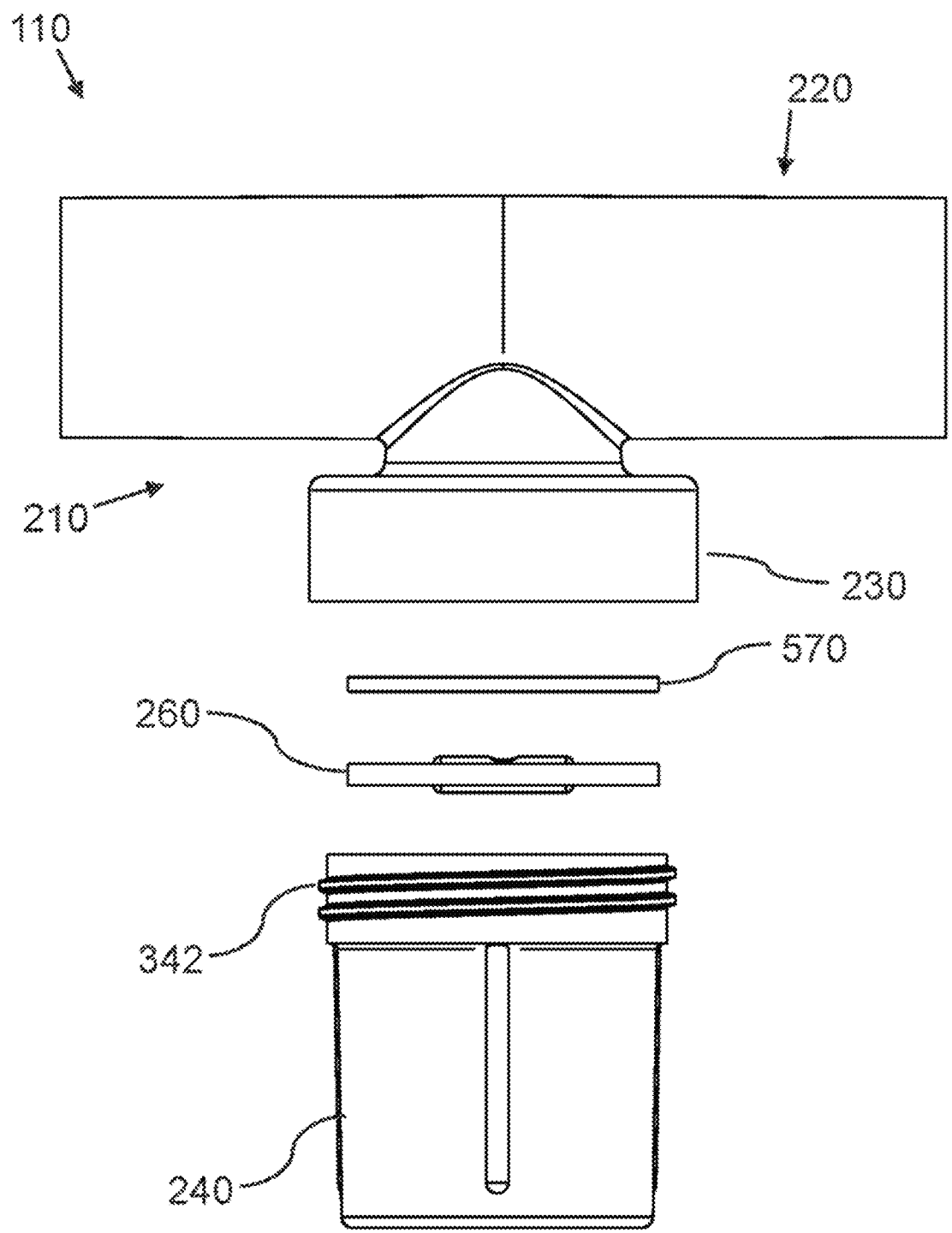
FIG. 5 is a front view of the inline drain sanitizing system of FIG. 1 according to an embodiment of the present disclosure.
Figure 6A:
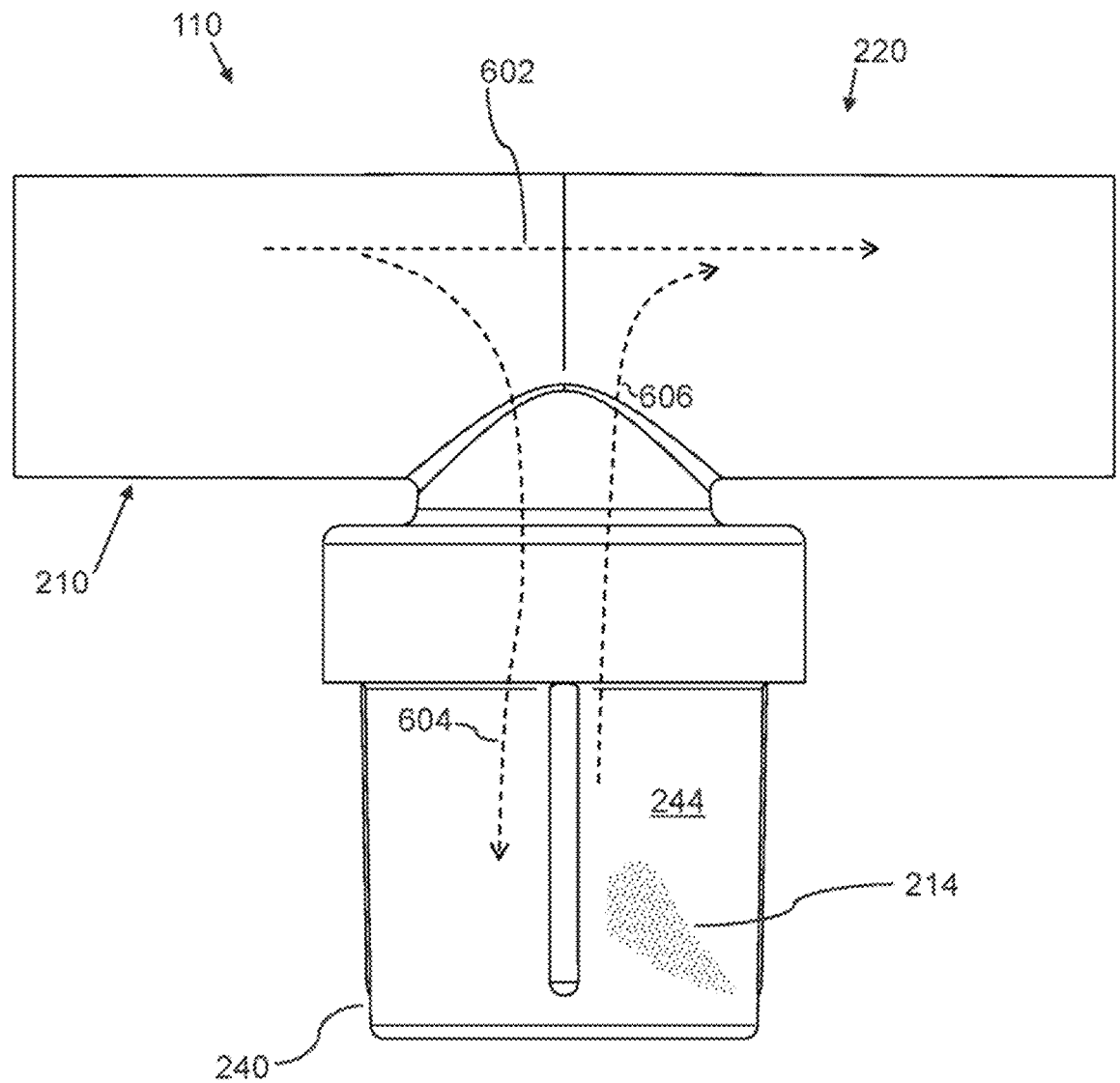
FIG. 6A is a front view of the inline drain sanitizing system of FIG. 1 according to an embodiment of the present disclosure.
Figure 6B:
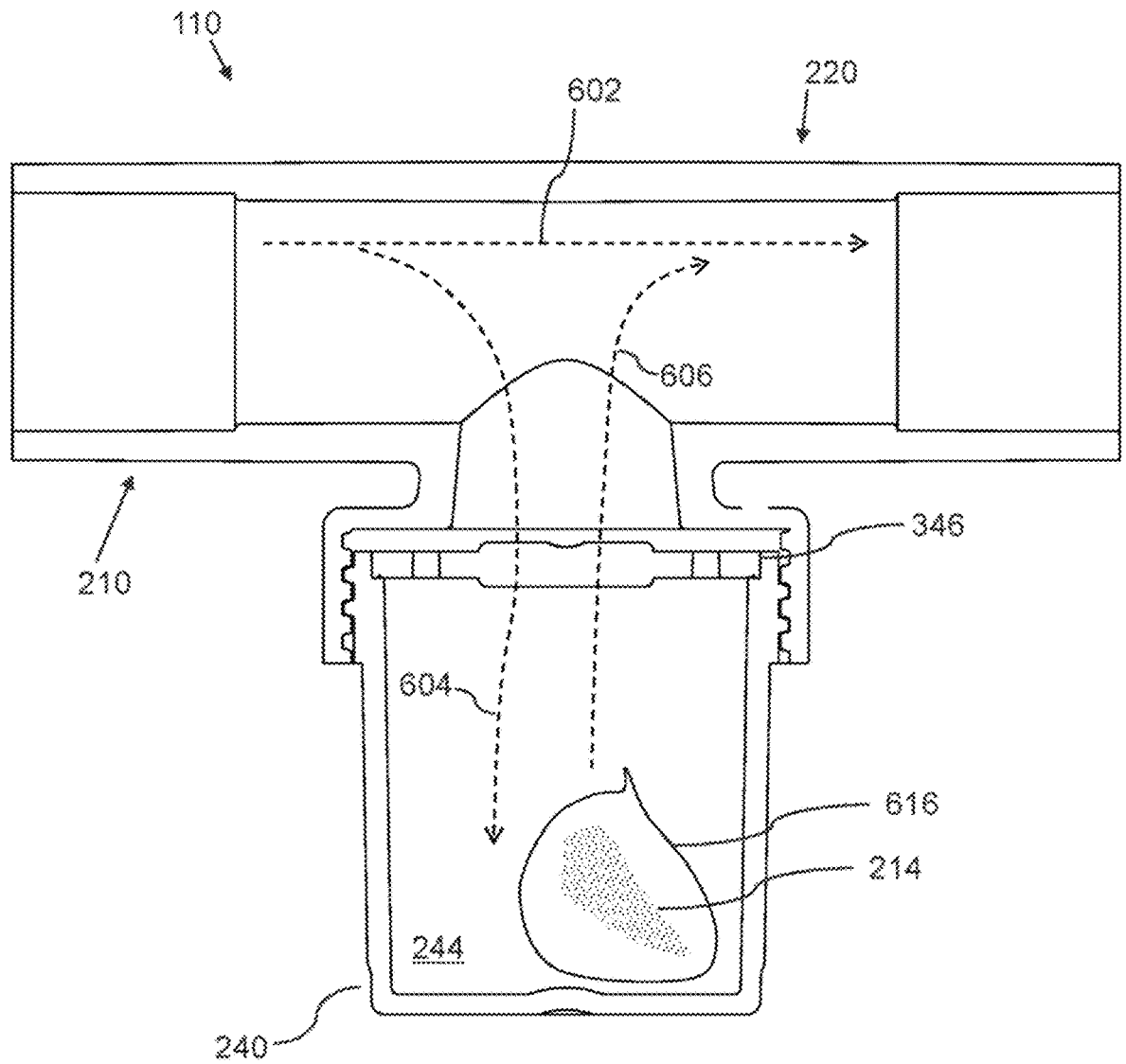
FIG. 6B is a cross-sectional front view of the inline drain sanitizing system of FIG. 1 according to an embodiment of the present disclosure.

Referring also to FIGS. 3A, 3B, 3C, an interior of treatment subsystem 112 may be in fluid contact with connector pipe segment 220 via treatment port 226, wherein the interior of treatment subsystem 112 may be configured to contain sanitizing composition 214. An upper end of container body 240 may include line connector 342, which may be configured to detachably connect to a lower end of container connector 230 to create a tight lock. For example, the upper end of container body 240 may be configured with line connector 342 (e.g., a snap-lock connector with snap lock tabs or a threaded connector that includes screw-in threading) that may lock or screw into (or onto) the lower end of container connector 230. This connection of container body 240 and line connector 342 may be airtight and may work with a pressured configuration of condensate drain line 194. Sanitizing composition 214 may be positioned within interior 244 of container body 240.

Referring also to FIGS. 4, 5, 6A, 6B, sanitizing composition 214 may be configured as a tablet (e.g., a cylindrical tablet), wherein such a tablet may be configured to fit inside container body 240. Sealing plate 260 may be positioned in place on top of the container body 240 between the lower end of container connector 230 and container body 240. Sealing plate 260 may include at least one sealing aperture 262 to allow condensate fluid 186 to flow via at least one sealing aperture 262 (e.g., unsanitized condensate in the direction of arrow 604) into interior 244 of container body 240. Accordingly, condensate fluid 186 may mix with sanitizing composition 214, wherein sealing plate 260 may be permanently connected to container body 240. For example, sealing plate 260 may e.g., be sonic welded, glued, hot welded to container body 240. Accordingly, flow 602 of condensate fluid 186 past treatment port 226 may create drag that may cause condensate fluid 186 to be mixed with sanitizing composition 214 to flow (in the direction of arrow 606) as sanitized condensate into drain line 190.

Container body 240 may further include upper opening 341 and interior 244 that is accessible via upper opening 341. As discussed above, an upper end of container body 240 may be configured to detachably connect to a lower end of container connector 230 to create a tight lock; wherein condensate fluid 186 may flow (via the upper opening 341) into interior 244 of container body 240, such that condensate fluid 186 may mix with sanitizing composition 214. Accordingly, a flow of condensate fluid 186 past treatment port 226 in connector pipe segment 220 may cause condensate fluid 186 to be mixed with sanitizing composition 214 to flow back into connector pipe segment 220 and subsequently into condensate drain line 194.

Treatment subsystem 112 may further include sealing ring 570 (FIG. 5), which may be mounted between container body 240 and container connector 230. As discussed above, an upper end of container body 240 may be configured to detachably connect to a lower end of container connector 230 to create a tight lock. Treatment subsystem 112 may be configured with inside ledge 346 (FIG. 3) on an inner side of upper rim 344 of container body 240, such that sealing plate 260 may rest on inside ledge 346, wherein an upper surface of sealing plate 260 may be flush with an upper surface of upper rim 344 of container body 240. Sealing ring 570 may be positioned between sealing plate 260 and container connector 230.

The at least one sealing aperture 262 of sealing plate 260 may include a central aperture configured with cross-diagonal bar 264, which partitions central aperture 262. Inline drain sanitizing system 110 may further include dissolvable bag 616 (FIG. 6B), which may be positioned within interior 244 of container body 240. Dissolvable bag 616 may be configured to be dissolvable by condensate fluid 186, wherein dissolvable bag 616 may include sanitizing composition 214. Cross-diagonal bar 264 may be configured to prevent removal of dissolvable bag 616 (which includes sanitizing composition 214) from container body 240. Further, cross-diagonal bar 264 may be configured to prevent dissolvable bag 616 (which includes sanitizing composition 214) from floating upwards (e.g., from container body 240 into container connector 230) and blocking treatment port 226 and/or the container connector 230 during use of inline drain sanitizing system 110.

Dissolvable bag 616 may be constructed from water dissolvable paper, polymer, or any other water dissolvable material. Sealing plate 260 may further include disc-shaped peripheral member 266 (FIG. 3A), which may include central aperture. As discussed above, the at least one sealing aperture 262 may include a central aperture. Sealing ring 570 may be disc-shaped, such that sealing ring 570 may be positioned on a top of disc-shaped peripheral member 266. Disc-shaped peripheral member 266 may include plurality of sealing apertures 268, such that plurality of sealing apertures 268 may aid in detachment of container body 240 from container connector 230 by e.g., reducing a suction effect between sealing ring 570 and disc-shaped peripheral member 266. Plurality of sealing apertures 268 may be equidistantly distributed around disc-shaped peripheral member 266. Plurality of sealing apertures 262 may each have a diameter in a range of e.g., 0.1 to 10 mm or 0.5 to 10 mm.

Manifold assembly 210 and/or container body 240 may be made of a transparent material such that inline drain sanitizing system 110 may provide visibility to the flow of condensate fluid 186 and/or the status of sanitizing composition 214. An example such a transparent material may include but is not limited to a transparent plastic material (e.g., polymethylmethacrylate, cellulose acetate butyrate, polycarbonate, or glycol modified polyethylene terephthalate).

Examples of sanitizing composition 214 may include but are not limited to: a powdered sanitizing composition (that may be water soluble so that the powdered sanitizing composition may dissolve in condensate fluid 186 and may include cleaning/disinfectanting/sanitizing/antimicrobial agents and/or materials); a granular sanitizing composition (that may be water soluble so that the granular sanitizing composition may dissolve in condensate fluid 186 and may include cleaning/disinfectanting/sanitizing/antimicrobial agents and/or materials); a blocked/pelleted/tableted sanitizing composition (that may be water soluble so that this solid sanitizing composition may dissolve in condensate fluid 186 and may include cleaning/disinfectanting/sanitizing/antimicrobial agents and/or materials); a liquid sanitizing composition (that may be water soluble so that the liquid sanitizing composition may dissolve in condensate fluid 186 and may include cleaning/disinfectanting/sanitizing/antimicrobial agents and/or materials); and a gel sanitizing composition (that may be water soluble so that the gel sanitizing composition may dissolve in condensate fluid 186 and may include cleaning/disinfectanting/sanitizing/antimicrobial agents and/or materials).

Examples of sanitizing composition 214 may include but are not limited to a powdered/granular/solid/liquid/gel form of e.g., quaternary ammonium chloride, chlorine, bromine, Biguanide, silver nitrate (or combinations thereof).

Figure 7:
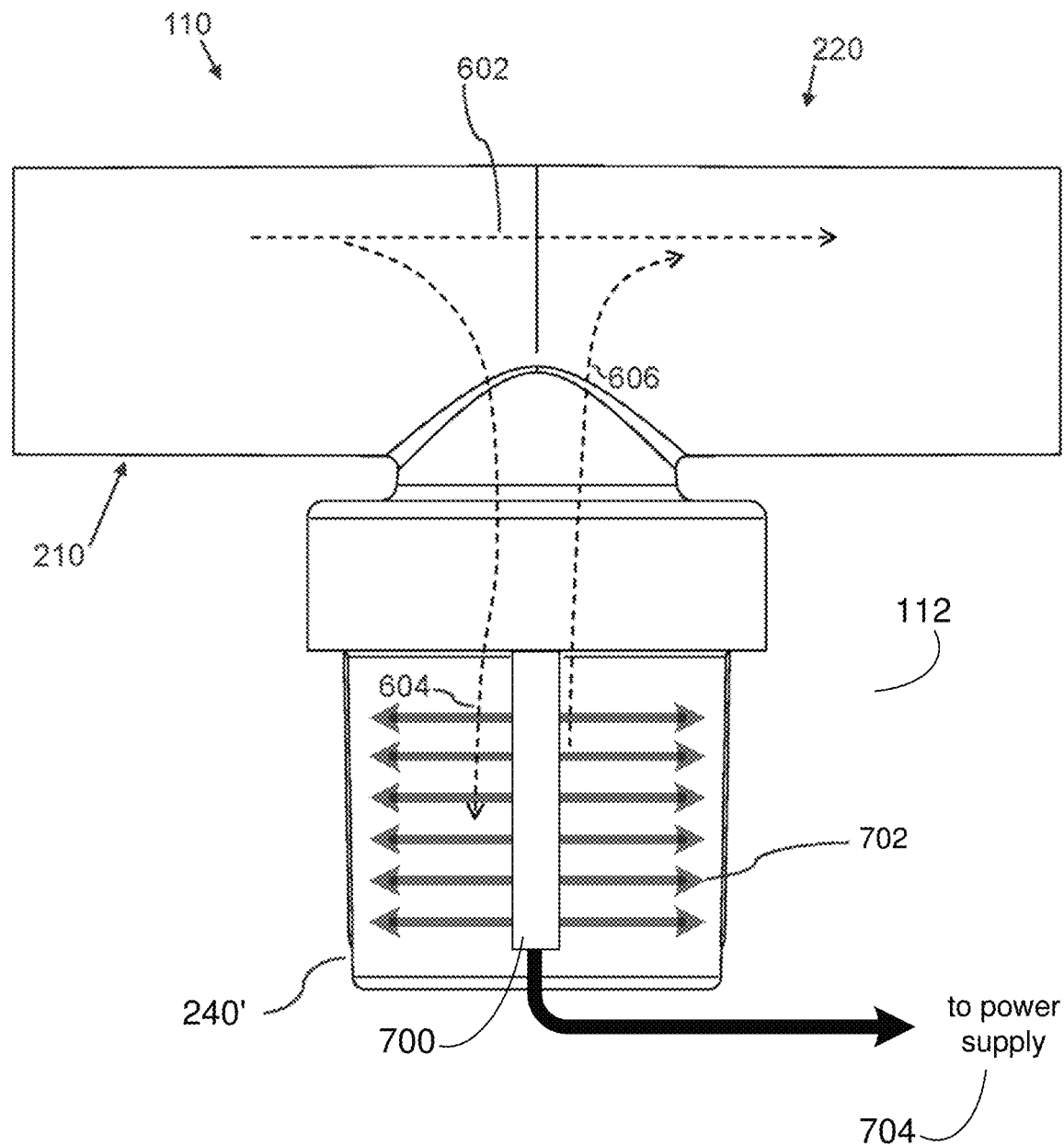
FIG. 7 is a front view of the inline drain sanitizing system of FIG. 1 according to an embodiment of the present disclosure.

As discussed above and referring also to FIG. 7, inline drain sanitizing system 110 may include treatment subsystem 112. As will be discussed below in greater detail, treatment subsystem 112 may be configured to utilize a light-based treatment system to sanitize the unsanitized condensate (e.g., condensate fluid 186). For example, treatment subsystem 112 may include container body 240' that may include light source 700 configured to generate ultraviolet light (e.g., ultraviolet light 702). Container body 240 may be configured to be couplable to a power source (e.g., power source 704) that provides electrical power to light source 700. Treatment subsystem 112 may be configured to allow the unsanitized condensate (e.g., condensate fluid 186) to interact with the ultraviolet light (e.g., ultraviolet light 702) such that ultraviolet light 702 may sanitize condensate fluid 186 and condensate drain line 194.

Here has thus been described a multitude of embodiments of inline drain sanitizing system 110, and systems and methods related thereto, which can be employed in numerous modes of usage. The many features and advantages of the invention are apparent from the detailed specification, and thus, it is intended by the appended claims to cover all such features and advantages of the invention, which fall within the true spirit and scope of the invention. For example, in related embodiments, inline drain sanitizing system 110 may be configured for installation on a vertical drain line or vertical pipe, for example such that container connector 230 includes a 90-degree bend (not shown) in order to maintain a vertical orientation of treatment subsystem 112.

Many such alternative configurations are readily apparent and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

General

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. An inline drain sanitizing system, comprising:
    a manifold assembly including an inlet port, an outlet port, and a treatment port, wherein:
        the inlet port is configured to be couplable to a condensate supply line and receive unsanitized condensate, and
        the outlet port is configured to be couplable to a condensate drain line and provide sanitized condensate; and
    a treatment subsystem configured to interface with the treatment port and process the unsanitized condensate to generate the sanitized condensate, wherein the treatment subsystem is configured to be disposed below the condensate supply line and the condensate drain line, and wherein the treatment subsystem is disposed outside of a flow path of the condensate supply line and the condensate drain line to not impede a flow rate and performance of the condensate drain line.

2. The inline drain sanitizing system of claim 1 wherein the manifold assembly is constructed of a transparent material to allow for the monitoring of condensate flow.

3. The inline drain sanitizing system of claim 1 wherein the treatment subsystem is configured to be removably attachable to the manifold assembly.

4. The inline drain sanitizing system of claim 1 wherein the treatment subsystem is configured to be threadably attachable to the manifold assembly.

5. The inline drain sanitizing system of claim 1 wherein the treatment subsystem is configured to utilize a chemical-based treatment system to sanitize the unsanitized condensate.

6. The inline drain sanitizing system of claim 5 wherein the chemical-based treatment system is configured to contain a sanitizing composition.

7. The inline drain sanitizing system of claim 6 wherein the sanitizing composition is contained within a dissolvable bag.

8. The inline drain sanitizing system of claim 6 wherein the treatment subsystem is configured to allow the unsanitized condensate to interact with the sanitizing composition to generate the sanitized condensate.

9. The inline drain sanitizing system of claim 6 wherein the treatment subsystem is constructed of a transparent material to allow for the monitoring of the sanitizing composition.

10. The inline drain sanitizing system of claim 6 wherein the sanitizing composition includes silver nitrate.

11. The inline drain sanitizing system of claim 10 wherein the sanitizing composition includes one or more of:
    a powered sanitizing composition;
    a granular sanitizing composition;
    a solid sanitizing composition;
    a gel sanitizing composition; and
    a liquid sanitizing composition.

12. The inline drain sanitizing system of claim 11 wherein the light-based treatment system is configured to generate ultraviolet light.

13. The inline drain sanitizing system of claim 12 wherein the treatment subsystem is configured to allow the unsanitized condensate to interact with the ultraviolet light to generate the sanitized condensate.

14. The inline drain sanitizing system of claim 1 wherein the treatment subsystem is configured to utilize a light-based treatment system to sanitize the unsanitized condensate.

15. The inline drain sanitizing system of claim 1 wherein the condensate supply line is configured to be coupled to an air conditioning unit.

16. The inline drain sanitizing system of claim 1 wherein the condensate drain line is configured to discharge the sanitized condensate.

17. An inline drain sanitizing system, comprising:
    a manifold assembly including an inlet port, an outlet port, and a treatment port, wherein:
        the inlet port is configured to be couplable to a condensate supply line and receive unsanitized condensate, and
        the outlet port is configured to be couplable to a condensate drain line and provide sanitized condensate; and
    a treatment subsystem configured to interface with the treatment port and process the unsanitized condensate to generate the sanitized condensate, wherein the treatment subsystem is configured to be disposed below the condensate supply line and the condensate drain line, and wherein the treatment subsystem is disposed outside of a flow path of the condensate supply line and the condensate drain line to not impede a flow rate and performance of the condensate drain line;
    wherein the treatment subsystem is configured to be threadably attachable to the manifold assembly and to utilize a chemical-based treatment system to sanitize the unsanitized condensate.

18. The inline drain sanitizing system of claim 17 wherein the manifold assembly is constructed of a transparent material to allow for the monitoring of condensate flow.

19. The inline drain sanitizing system of claim 17 wherein the chemical-based treatment system is configured to contain a sanitizing composition.

20. The inline drain sanitizing system of claim 19 wherein the sanitizing composition is contained within a dissolvable bag.

21. The inline drain sanitizing system of claim 19 wherein the treatment subsystem is configured to allow the unsanitized condensate to interact with the sanitizing composition to generate the sanitized condensate.

22. The inline drain sanitizing system of claim 19 wherein the treatment subsystem is constructed of a transparent material to allow for the monitoring of the sanitizing composition.

23. The inline drain sanitizing system of claim 19 wherein the sanitizing composition includes silver nitrate.

24. The inline drain sanitizing system of claim 19 wherein the sanitizing composition includes one or more of:
   a powered sanitizing composition;
   a granular sanitizing composition;
   a solid sanitizing composition;
   a gel sanitizing composition; and
   a liquid sanitizing composition.

25. The inline drain sanitizing system of claim 17 wherein the condensate supply line is configured to be coupled to an air conditioning unit.

26. The inline drain sanitizing system of claim 17 wherein the condensate drain line is configured to discharge the sanitized condensate.

27. An inline drain sanitizing system, comprising:
   a manifold assembly including an inlet port, an outlet port, and a treatment port, wherein:
      the inlet port is configured to be couplable to a condensate supply line and receive unsanitized condensate, and
      the outlet port is configured to be couplable to a condensate drain line and provide sanitized condensate; and
   a treatment subsystem configured to interface with the treatment port and process the unsanitized condensate to generate the sanitized condensate using a gel chemical-based sanitizing composition, wherein the treatment subsystem is configured to be disposed below the inlet port and the outlet port, and wherein the treatment subsystem is disposed outside of a flow path of the inlet port and the outlet port to not impede a flow rate and performance of the condensate drain line;
   wherein:
   the treatment subsystem is configured to be threadably attachable to the manifold assembly and to utilize a chemical-based treatment system to sanitize the unsanitized condensate, wherein the chemical-based treatment system is configured to contain the gel sanitizing composition,
   the condensate supply line is configured to be coupled to an air conditioning unit, and
   the condensate drain line is configured to discharge the sanitized condensate.

28. The inline drain sanitizing system of claim 27 wherein the sanitizing composition is contained within a dissolvable bag.

29. The inline drain sanitizing system of claim 27 wherein the treatment subsystem is configured to allow the unsanitized condensate to interact with the sanitizing composition to generate the sanitized condensate.

* * * * *